US005874575A

United States Patent [19]
Fuchs et al.

[11] Patent Number: 5,874,575
[45] Date of Patent: *Feb. 23, 1999

[54] PREPARATION OF CAPROLACTAM

[75] Inventors: Eberhard Fuchs, Frankenthal; Guenther Achhammer, Mannheim, both of Germany

[73] Assignee: BASF Aktiengesellschaft, Ludwigshafen, Germany

[ * ] Notice: The term of this patent shall not extend beyond the expiration date of Pat. No. 5,495,016.

[21] Appl. No.: 725,438

[22] Filed: Oct. 3, 1996

Related U.S. Application Data

[63] Continuation of Ser. No. 358,414, Dec. 19, 1994, abandoned.

[30] Foreign Application Priority Data

Dec. 3, 1994 [DE] Germany .......................... 44 43 125.2

[51] Int. Cl.$^{6}$ ............................ C07D 201/08; B01D 3/00

[52] U.S. Cl. ............................ 540/539; 540/540; 203/73; 203/78; 203/DIG. 16; 203/DIG. 25

[58] Field of Search .............................. 203/73, DIG. 16, 203/36–37, 38, 29, 76, 14, 77–78, DIG. 25; 540/540, 539

[56] References Cited

U.S. PATENT DOCUMENTS

| | | | |
|---|---|---|---|
| 2,301,964 | 11/1942 | Martin | 540/539 |
| 4,625,023 | 11/1986 | Mares et al. | 540/539 |
| 4,764,607 | 8/1988 | Balint et al. | 203/57 |
| 4,767,503 | 8/1988 | Crescentini et al. | 203/96 |
| 4,767,857 | 8/1988 | Merger et al. | 540/538 |
| 5,495,014 | 2/1996 | Fuchs et al. | 540/538 |
| 5,495,016 | 2/1996 | Achhammer et al. | 540/539 |
| 5,496,941 | 3/1996 | Ritz et al. | 540/539 |
| 5,646,277 | 7/1997 | Fuchs et al. | 540/539 |

*Primary Examiner*—Virginia Manoharan
*Attorney, Agent, or Firm*—Keil & Weinkauf

[57] ABSTRACT

An improved process for the preparation of caprolactam by heating 6-aminocapronitrile in the presence of a heterogenous catalyst and water under superatmospheric pressure without rapid deactivation of the catalysts used. The process further includes the addition of a low or high boiling alcohol in the heating phase, after which the products are obtained by distillation. The process further includes a method of working up the top and bottom products of the reactors to achieve higher yields.

23 Claims, No Drawings

PREPARATION OF CAPROLACTAM

This application is a continuation of application Serial No. 08/358.414, filed on Dec. 19, 1994 now abandoned.

The present invention relates to an improved process for the preparation of caprolactam by heating 6-aminocapronitrile in the presence of a heterogeneous catalyst and water under super-atmospheric pressure.

Several patents and literature publications disclose the preparation of 6-aminocapronitrile by hydrogenation of one of the nitrile groups of adiponitrile. The use of Raney nickel is described, for example, in DE 836 938, DE 848 654 (both BASF) and U.S. Pat. No. 5,151,543 (DuPont). Kinetic investigations are described by C. Mathieu et al., Chem. Eng. Sci. 47 (1992), 2289–2294.

U.S. Pat. No. 4,628,085 (Allied) describes the reaction of 6-aminocapronitrile with water in the gas phase over a special acidic silica gel (Porasil A) at 300° C. By diluting 1.9 % of substrate with water (14 %), ammonia (6.3 %) and hydrogen/nitrogen, caprolactam can be obtained in a quantitative conversion with a selectivity of over 95 %, but a noticeable decrease in the conversion and selectivity by at least 5 % each takes place within only 150 hours as a result of deactivation.

A similar gas-phase process is also described in U.S. Pat. No. 4,625,023 (Allied). Here, a highly dilute gas stream of 6-aminocapronitrile, adiponitrile, ammonia, water and carrier gas is passed over a silica gel and a copper/chromium/barium-titanium oxide catalyst bed. The caprolactam selectivity is 91 % at 85 % conversion. The problem of catalyst deactivation is discussed and measures for reducing this are carried out but no information is given with regard to their success.

These processes both have the disadvantage of rapid catalyst deactivation. This problem is not solved.

U.S. Pat. No. 2,245,129 (DuPont) describes the preparation of linear polyamides by heating a 50 % strength aqueous solution of 6-aminocapronitrile to 220° C. for 20 hours. There is no information about the formation of caprolactam.

On the other hand, U.S. Pat. No. 2,301,964 describes the uncatalyzed conversion of aminocapronitrile (as an aqueous solution) to caprolactam at 285° C. The yield is substantially below 80 %, and a residue which is not further described is obtained.

FR-A 2 029 540 describes a process for the cyclization of 6-aminocapronitrile to caprolactam by means of catalysts, the catalysts used being metallic Zn or Cu powder or oxides, hydroxides, halides or cyanides of rubidium, of lead, of mercury or of the elements having atomic numbers from 21 to 30 or from 39 to 48. The catalysts described are used as suspension catalysts in batchwise stirred autoclaves. Caprolactam is obtained in yields of up to 83 %. However, separating off the catalysts completely from the desired product caprolactam presents problems since caprolactam can form compounds with the soluble components of the metals used, or very fine particles may form as a result of mechanical stirring.

It is known that 6-aminocaproic acid, dissolved in water (U.S. Pat. No. 3,485,821), can be cyclized to caprolactam at 150°–350° C.

DE-C 952 442 discloses a process in which caprolactam is obtained in addition to aminocaproates by amination of 5-formylvalerates under hydrogenating conditions in two stages.

U.S. Pat. No. 3,988,319 (cf. also DE 2 535 689) describes a process for the cyclization of 6-aminocaproic acid in methanol or ethanol as a solvent. In order to avoid secondary reactions of the 6-aminocaproic acid, however, the amino acid must be brought into solution so slowly that it does not accumulate as a solid. Temperatures of about 170° C. are required for this purpose. Furthermore, the water content of the solution must not exceed 40 %, since otherwise open-chain polymers form. The water of reaction liberated must be separated off when the alcohol is reused.

However, the authors of U.S. Pat. No. 3,988,319 also state in Ind. Eng. Chem. Process Des. Dev. 17 (1978), 9–16, that the cyclization of 6-aminocaproic acid in water to caprolactam leads to significant amounts of oligomers unless concentrations below 13 % and temperatures of about 300° C. are used.

A. Blade-Font, Tetrahedron Lett. 21 (1980), 2443–2446, describes the cyclization of 6-aminocaproic acid as a suspension in toluene in the presence of alumina or silica gel with removal of the water of reaction. For complete desorption of the caprolactam, the catalyst must be washed with methylene chloride/methanol and polymers precipitated with diethyl ether. The yield of caprolactam after a reaction time of 20 hours is 82 % over alumina and 75 % over silica gel.

EP 271 815 describes the cyclization of 6-aminocaproates to caprolactam by dissolving the ester in an aromatic hydrocarbon, carrying out cyclization at from 100° to 320° C. and at the same time separating off the alcohol eliminated.

EP-A 376 122 describes the cyclization of 6-aminocaproates to caprolactam by dissolving the ester in an aromatic hydrocarbon and carrying out cyclization with the additional use of water at from 230° to 350° C., in particular from 260° to 340° C.

It is known that polyamide 6 can be cleaved to obtain caprolactam. The cleavage is carried out under the action of acidic or basic catalysts at elevated temperatures, frequently in the presence of steam, ie. at low pressure. Chem. Ing. Techn. 45 (1973), 1510 describes the technical procedure for a cleavage process with superheated steam, it being necessary to concentrate a caprolactam/water solution for working up. In EP 209021, the cleavage is carried out in a fluidized alumina bed. EP 529 470 has potassium carbonate as a catalyst for the polyamide 6 cleavage and carries out the reaction at from 250° to 320° C. with simultaneous removal of the caprolactam by distillation under reduced pressure.

The disadvantages of all processes to date for the cleavage of polyamide 6 to caprolactam are the very energy-consumptive separation of large amounts of water and the removal of catalysts, such as phosphoric acids and salts thereof, potassium carbonate or alkali metal oxides. In the case of the gas-phase reactions, the polymer is heated to, as a rule, 270°–400° C. and is cleaved together with water in a fluidized-bed reactor. The formation of byproducts and deactivation due to agglomeration of the catalyst bed are the result.

It is an object of the present invention to provide an improved process for the preparation of caprolactam starting from 6-aminocapronitrile, which can be carried out in a technically feasible manner with high selectivity and without the problems of rapid deactivation of the catalysts used. Furthermore, the process should be capable of being carried out without significant production of low boilers and/or high boilers.

We have found that this object is achieved by a process for the preparation of caprolactam by heating 6-aminocapronitrile in the presence of a heterogeneous catalyst and water under superatmospheric pressure, wherein (a) 6-aminocapronitrile, or a mixture containing essentially 6-aminocapronitrile, and water and a low-boiling or a high-boiling alcohol are heated in the presence of a heterogeneous catalyst in a reactor A to give a mixture I, (b) mixture I is then distilled to give a top fraction, caprolactam and a bottom product, ammonia being removed before the distillation if it is present in mixture I, and then (c1) the top fraction is fed into the reactor A of stage (a), if desired the top fraction being mixed with the alcohol and/or water and/or 6-aminocapronitrile used in stage (a) before being fed into the reactor A, or (c2) the top fraction, if desired with the bottom product from stage (b), is fed into a reactor B, the top fraction being mixed, if desired, with the alcohol and/or water and/or 6-aminocapronitrile used in stage (a) before being fed into the reactor B, and caprolactam is then obtained similarly to stage (b) by distillation, and either (d1) the bottom product from stage (b) is fed into the reactor A of stage (a) or (d2) if desired water and if desired a low-boiling or a high-boiling alcohol are added to the bottom product and the latter is then heated similarly to stage (a) in a further reactor C to give a reacted mixture, from which caprolactam is obtained by distillation, or (d3) water is added to the bottom product, which is then heated in a reactor D without the addition of a catalyst to give a reacted mixture, and caprolactam is obtained from said reacted mixture by distillation, or (d4) the bottom product to which water and a base have been added is heated in a reactor E to give a reacted mixture, from which caprolactam is obtained by distillation.

The 6-aminocapronitrile used according to the invention as starting material is usually obtained by hydrogenating adiponitrile by a known process, for example described in DE-A 836 938, DE-A 848 654 or U.S. Pat. No. 5,151,543.

It is also possible to introduce into the reactor A mixtures which may-contain essentially 6-aminocapronitrile and hexamethylenediamine, adiponitrile and/or caprolactam, as well as high-boiling fractions (high boilers), such as 6-aminocaproamide, 6-aminocaproic acid, polycaprolactam and oligomers of caprolactam and of further 6-aminocaproates which are obtained when working up the caprolactam prepared according to the invention, and the 6-aminocaproates may be either low-boiling or high-boiling, depending on the ester radical.

According to the invention, 6-aminocapronitrile is reacted with water, preferably from 0.01 to 35, particularly preferably from 1 to 10, mol of water being used per mol of 6-aminocapronitrile. According to the invention, a low-boiling or high-boiling alcohol is furthermore used, a dilution of from 1 to 50 % by weight of 6-aminocapronitrile being preferably chosen.

Low-boiling alcohols are those which, at 5 mbar, have a boiling point of not more than 10° C. below the boiling point of the caprolactam, for example $C_1$–$C_{10}$-alkanols, in particular methanol, ethanol, n-propanol, isopropanol, n-butanol, isobutanol or secbutanol, particularly preferably methanol or ethanol.

High-boiling alcohols are those which, at 5 mbar, have a boiling point at least 10° C. above the boiling point of the caprolactam, for example polyetherols, such as tetraethylene glycol.

In a further embodiment, from 0 to 5, preferably from 0.1 to 2 % by weight of ammonia and/or hydrogen and/or nitrogen may be added to the reaction mixture.

Examples of heterogeneous catalysts which may be used are: acidic, basic or amphoteric oxides of the elements of the second, third or fourth main group of the Periodic Table, such as calcium oxide, magnesium oxide, boron oxide, alumina, tin oxide or silica as pyrogenic silica, silica gel, kieselguhr, quartz or mixtures thereof, and oxides of metals of the second to sixth subgroups of the Periodic Table, such as titanium oxide, in amorphous form or as anatase or rutile, zirconium oxide, zinc oxide, manganese oxide or mixtures thereof. Oxides of the lanthanides and actinides, such as cerium oxide, thorium oxide, praseodymium oxide, samarium oxide, rare earth mixed oxides or mixtures thereof with abovementioned oxides may also be used. Further catalysts may be, for example: vanadium oxide, niobium oxide, iron oxide, chromium oxide, molybdenum oxide, tungsten oxide or mixtures thereof. Mixtures of the stated oxides with one another are also possible. Some sulfides, selenides and tellurides, such as zinc telluride, tin selenide, molybdenum sulfide, tungsten sulfide and sulfides of nickel, of zinc and of chromium, may also be used.

The abovementioned compounds may be doped with compounds of main groups 1 to 7 of the Periodic Table or may contain these.

Zeolites, phosphates and heteropolyacids and acidic and alkaline ion exchangers, such as Naphion® are suitable catalysts and may also be used.

If required, these catalysts may contain up to 50 % by weight in each case of copper, tin, zinc, manganese, iron, cobalt, nickel, ruthenium, palladium, platinum, silver or rhodium.

Depending on the composition of the catalyst, the latter may be used as unsupported or supported catalysts. For example, titanium dioxide may be used as titanium dioxide extrudes or as titanium dioxide applied in a thin layer on a carrier. All methods described in the literature may be used for applying $TiO_2$ to a carrier such as silica, alumina or zirconium dioxide. Thus, a thin $TiO_2$ layer can be applied by hydrolysis of titanium organyls, such as titanium isopropylate or titanium butylate, or by hydrolysis of $TiCl_4$ or other inorganic titanium-containing compounds. Soles containing titanium oxide may also be used.

According to the invention, the reaction in stage (a) is carried out at from 100° to 320° C., preferably from 160° to 280° C., particularly preferably from 180° to 260° C.

Usually, the reaction in stage (a) is carried out under superatmospheric pressure, the pressure being chosen as a rule to be from 0.1 to 50, preferably from 0.5 to 25, MPa.

The duration of the reaction in reactor A depends essentially on the chosen process parameters and, in the continuous process, is in general from 1 to 300, preferably from 5 to 120, minutes. The conversion generally decreases in the case of shorter reaction times, while observations to date have shown that longer reaction times result in increased formation of oligomers, so that larger amounts of oligomers would have to be recycled for cleavage.

The cyclization (stage (a)) is preferably carried out continuously in a reactor A, preferably in a tube reactor, in a stirred kettle or in a combination thereof.

The cyclization (stage (a)) may also be carried out batchwise. The reaction time in this case is usually from 30 to 300 minutes.

According to the invention, the discharge from reactor A is a mixture I consisting essentially of water, alcohol, 6-aminocaproates obtained by reaction of 6-aminocaproic acid formed during the reaction and the alcohol used, caprolactam, ammonia 5 and high-boiling compounds (high boilers), such as 6-aminocaproamide and oligomers of caprolactam.

According to the invention, in stage (b) mixture I is distilled by a conventional method to give a top fraction, caprolactam and a bottom product. If the mixture I from stage (a) contains ammonia, the latter is, according to the invention, removed before the distillation. The ammonia can be removed by a conventional method, for example by distillation or by passing an inert gas stream through mixture I.

Working up of the mixture I can be carried out gradually or simultaneously, for example in a preferred embodiment by first removing the water and any low-boiling alcohol distilling azeo-tropically therewith by distillation and subjecting the resulting residue to one or more further distillations, or by distilling mixture I in a single distillation column.

In a preferred embodiment, first a distillation is carried out under reduced pressure at from 10 to 500, preferably 50 to 350, mbar to give water and possibly alcohol and a distillation residue, which is subjected to a further distillation at from 90° to 220° C., preferably from 100° to 160° C., at from 0.01 to 1, preferably from 0.5 to 300, mbar to give a top fraction, caprolactam and a bottom product.

The top fraction consists as a rule of essentially low-boiling alkyl 6-aminocaproates, unconverted 6-aminocapronitrile and, unless already removed separately, water and the alcohol used, if it is low-boiling.

As a rule, the bottom product is essentially composed of high-boiling components, such as oligomers of caprolactam, 6-aminocaproamide, 6-aminocaproic acid and, depending on the alcohol used, high-boiling 6-aminocaproates and, if used, high-boiling alcohol.

According to the invention, the top fraction, if desired together with any alcohol and water separated off beforehand, is recycled to the reactor A (stage (c1)), and the top fraction may be mixed with the alcohol and/or water and/or 6-aminocapronitrile used in stage (a) before being fed into the reactor A.

According to the invention, the top fraction obtained in stage (b) may optionally be fed into a reactor B (stage (c2)), if desired with the bottom product from stage (b) and if desired together with any alcohol and water separated off beforehand, and the top fraction may be mixed with the alcohol and/or water and/ or 6-aminocapronitrile used in stage (a) before being fed into the reactor B. The reaction conditions in reactor B are chosen so that they correspond to those in reactor A. The reacted mixture from reactor B is worked up similarly to stage (b), caprolactam being obtained in one or more distillation stages.

In addition to the abovementioned variants, the bottom product obtained in stage (b) can be worked up in stage (c2), according to the invention, by four other methods, either in stage (d1) the bottom product from stage (b) being fed into the reactor A of stage (a) or in stage (d2), if desired, water and, if desired, a low-boiling or high-boiling alcohol being added to the bottom product, preferably a 0.1- to 25-fold, particularly preferably a 0.15- to 15-fold, weight of water and preferably a 1- to 25-fold, particularly preferably a 3- to 15-fold, weight of alcohol, and heating then being carried out similarly to stage (a) in a further reactor c to give a reacted mixture, from which caprolactam is obtained by distillation, preferably similarly to stage (b), or (d3) water being added to the bottom product, preferably a 5- to 25-fold, particularly preferably a 7- to 15-fold, weight of water, and heating being carried out without the addition of a catalyst in a reactor D, where the reaction conditions are preferably chosen to be similar to those in reactor A I [sic], except that the temperature is chosen to be from 200° to 350° C., preferably from 280° to 320° C., and the residence time to be from 5 to 240 minutes, to give a reacted mixture, from which caprolactam is obtained by distillation, preferably similarly to stage (b), or (d4) the bottom product to which water and a base have been added being heated in a reactor E to give a reacted mixture, from which caprolactam is obtained by distillation, preferably similarly to stage (b), heating of the bottom product preferably being effected under reduced pressure at in general from 0.1 to 50, preferably from 1 to 10, mbar, in the presence of 45 the base, as a rule from 1 to 10, preferably from 1 to 3, % by weight thereof, in reactor E, preferably a tube reactor, at from 200° to 400° C., preferably from 280° to 320° C.

In principle, the bottom product can of course also be worked up by prior art methods, for example by subjecting it to one of the conventional gas-phase processes or to one of the usual working-up methods with acidic catalysts. However, owing to the disadvantages of the prior art processes, the abovementioned novel embodiments (c2) and (d1) to (d4) are preferred.

The bases used are preferably alkali metal hydroxides and alkali metal carbonates, such as sodium hydroxide, potassium hydroxide, sodium carbonate and potassium carbonate, or a mixture thereof, particularly preferably sodium hydroxide and/or potassium hydroxide.

The advantage of the novel process is that caprolactam is obtained in a technically feasible manner with high selectivity and in high yield starting from 6-aminocapronitrile without the problems of rapid deactivation of the catalysts used, no significant amounts of low boilers and high boilers being produced.

EXAMPLES

Example 1

(a) 70 ml/h of a solution of 10 % by weight of 6-aminocapronitrile, 3.2 % by weight of water and ethanol (remainder) were from [sic] at 100 bar into a tube reactor heated to 230° C., having a capacity of 20 ml, a diameter of 6 mm and a length of 710 mm and filled with titanium oxide (anatase) in the form of 1.5 mm extrudates.

The quantitative gas chromatographic evaluation of the reacted mixture gave the following yields (without ethanol and water): 91 % of caprolactam, 4 % of ethyl 6-aminocaproate and 1 % of 6-aminocapronitrile.

A product stream collected over 200 hours was freed from ethanol and water, and the resulting crude lactam was distilled. 56 g of low-boiling components (low boilers) and 126 g of high-boiling components (high boilers) and 1232 g of caprolactam were obtained. The low boilers essentially consisted of ethyl 6-aminocaproate and unconverted 6-aminocapronitrile, and the high boilers essentially consisted of oligomers.

(b) 445 g of water were added to 126 g of oligomers, 56 g of low boilers (from (a)) and 1200 g of 6-aminocapronitrile, and the mixture was diluted with ethanol to give a 10 % strength by weight solution. This solution was once again pumped at a rate of 70 ml/h through the reactor at 230° C. and 100 bar. The yields of the discharged product were determined by means of gas chromatographic analysis (calculated without ethanol and water) and were: 87 % of caprolactam, 3 % of ethyl 6-aminocaproate and 0.5 % of 6-aminocapronitrile.

After distillation, 1182 g of caprolactam, 36 g of low boilers and 150 g of high boilers were obtained from the second discharge. Altogether, 36 g of recyclable low boilers, 150 g of high boilers and 2432 g of caprolactam were obtained from 2600 g of 6-aminocapronitrile. The total yield was 93 % and the selectivity was 98 %.

Example 2

(a) 100 ml/h of a solution of 10 % by weight of 6-aminocapronitrile, 16.0 % by weight of water and ethanol (remainder) were from [sic] at 200 bar into a tube reactor heated to 260° C., having a capacity of 20 ml, a diameter of 6 mm and a length of 710 mm and filled with titanium oxide (anatase) in the form of 1.5 mm extrudates.

The quantitative gas chromatographic evaluation of the reacted mixture gave the following yields (without ethanol and water): 93 % of caprolactam and 2 % of ethyl 6-aminocaproate.

A product stream collected over 200 hours was freed from ethanol and water, and the resulting crude lactam was distilled. 55 g of low-boiling components (low boilers) and 140 g of high-boiling components (high boilers) and 1820 g of caprolactam were obtained. The low boilers essentially consisted of ethyl 6-aminocaproate, and the high boilers essentially consisted of oligomers.

(b) 3830 g of water were added to 140 g of oligomers, 55 g of low boilers (from Example 2a) and 2200 g of 6-aminocapronitrile, and the mixture was diluted with ethanol to give a 10 % strength by weight solution. This solution was once again pumped at a rate of 100 ml/h through the reactor at 260° C. and 200 bar. The yields of the discharged product were determined by means of gas chromatographic analysis (calculated without ethanol and water) and were: 91 % of caprolactam and 2 % of ethyl 6-aminocaproate.

After distillation, 2129 g of caprolactam, 57 g of low boilers and 196 g of high boilers were obtained from the second discharge.

Altogether, 57 g of recyclable low boilers, 196 g of high boilers and 3945 g of caprolactam were obtained from 4200 g of 6-aminocapronitrile. The total yield was 94 % and the selectivity was 99 %.

Example 3

(a) 15 ml/h of a solution of 10 % by weight of 6-aminocapronitrile, 3.2 % by weight of water and ethanol (remainder) were from [sic] at 100 bar into a tube reactor heated to 200° C., having a capacity of 20 ml, a diameter of 6 mm and a length of 710 mm and filled with titanium oxide (anatase) in the form of 1.5 mm extrudates.

The quantitative gas chromatographic evaluation of the reacted mixture gave the following yields (without ethanol and water): 88 % of caprolactam, 4 % of ethyl 6-aminocaproate and 4 % of 6-aminocapronitrile.

A product stream collected over 200 hours was freed from ethanol and water, and the resulting crude lactam was distilled. 29 g of low-boiling components (low boilers) and 12 g of high-boiling components (high boilers) and 260 g of caprolactam were obtained. The low boilers essentially consisted of ethyl 6-aminocaproate and unconverted 6-aminocapronitrile, and the high boilers essentially consisted of oligomers.

(b) 94 g of water were added to 12 g of oligomers, 29 g of low boilers (from Example 3a) and 260 g of 6-aminocapronitrile, and the mixture was diluted with ethanol to give a 10 % strength by weight solution. This solution was once again pumped at a rate of 100 ml/h through the reactor at 250° C. and 200 bar. The yields of the discharged product were determined by means of gas chromatographic analysis (calculated without ethanol and water) and were: 91 % of caprolactam and 2 % of ethyl 6-aminocaproate.

After distillation, 265 g of caprolactam, 83 g of low boilers and 25 g of high boilers were obtained from the second discharge.

Altogether, 83 g of recyclable low boilers, 25 g of high boilers and 525 g of caprolactam were obtained from 560 g of 6-aminocapronitrile. The total yield was 94 % and the selectivity was 99 %.

We claim:

1. A process for the preparation of caprolantam comprising the following steps:

(a) heating 6-aminocapronitrile, or a mixture comprising 6-aminocapronitrile and water and a low-boiling or a high-boiling alcohol in the presence of a heterogenous catalyst under superatmospheric pressure in a reactor A to give a mixture I, (b) distilling the mixture I to give a top fraction, caprolactam, and a bottom product, (c1) feeding the top fraction into the reactor A of step (a), (c1') optionally mixing the top fraction of step (b) with the alcohol, water, or 6-aminocapronitrile of step (a) before feeding the top fraction into the reactor A, and (d1) feeding the bottom product from step (b) into the reactor A of stop (a).

2. The process of claim 1, wherein mixture I further comprises ammonia, and step (a) further comprises removing the ammonia prior to distilling in step (b).

3. The process of claim 1 wherein a temperature of from 100° to 320 ° C. is maintained in the reactor A.

4. The process of claim 1 wherein a pressure of from 0.1 to 50 MPa is maintained in the reactor A.

5. The process of claim 1 wherein from 0.01 to 35 mol of water are used per mol of 6-aminocapronitrile.

6. The process of claim 1 wherein a resident time of from 1 to 300 minutes is maintained in the reactor A.

7. The process of claim 1 wherein the alcohol is selected from the group consisting of methanol, ethanol, n-propanol, isopropanol, n-butanol, isobutanol, sec-butanol and tetraethylene glycol.

8. A process for the preparation of caprolactam comprising the following steps:

(a) heating 6-aminocapronitrile, or a mixture comprising 6aminocapronitrile and water, and a low-boiling or a high-boiling alcohol in the presence of a heterogenous catalyst under superatmospheric pressure in a reactor A to give a mixture I, (b) distilling the mixture I to give a top fraction, caprolactam and a bottom product, (c2) feeding the top fraction and optionally the bottom product into a reactor B to obtain a mixture from reactor B, and distilling the mixture from reactor B to yield further caprolactam, (C2') optionally mixing the top fraction with the alcohol, water, or 6-aminocapronitrile of step (a) before feeding into the reactor B, and (d1) feeding the bottom product from step (b) into the reactor A of step (a).

9. The process of claim 8, wherein a temperature of from 100° to 320° C. is maintained in the reactors.

10. The process of claim 8, wherein a pressure of from 0.1 to 50 MPa is maintained in the reactors.

11. The process of claim 8, wherein from 0.01 to 35 mol of water are used per mol of 6-aminocapronitrile in the mixture of 6-aminocapronitrile and water.

12. The process of claim 8, wherein a resident time of from 1 to 300 minutes is maintained in the reactors.

13. The process of claim 8, wherein the alcohol is selected from the group consisting of methanol, ethanol, n-propanol, isopropanol, n-butanol, isobutanol, sec-butanol and tetraethylene glycol.

14. A process for the preparation of caprolactam comprising the following steps:

(a) heating 6-aminocapronitrile, or a mixture comprising 6aminocapronitrile and water, and a low-boiling or a high-boiling alcohol in the presence of a heterogenous catalyst under superatmospheric pressure in a reactor A to give a mixture I, (b) distilling the mixture I to give a top fraction, caprolactam and a bottom product, (c1) feeding the top fraction into the reactor A of step (a), (c1') optionally mixing the top fraction from step (b) with the alcohol, water, or 6-aminocapronitrile of step (a) before feeding the top fraction into the reactor A, and (d2) adding a material selected from the group consisting of waters, a low-boiling alcohol, and a high-boiling alcohol to the bottom product to form a mixture and heating said mixture in a further reactor C to give a reacted mixture from which caprolactam is obtained by further distilling.

15. The process of claim 14 wherein the distilling in the step (d2) yields further caprolactam, a low-boiling fraction and a bottom product, and the step (d2) further comprises the step of recycling the low-boiling fraction to step (b).

16. The process of claim 14, wherein mixture I further comprises, ammonia, and step (a) further comprises removing the ammonia prior to distilling in step (b).

17. The process of claim 14 wherein the alcohol is selected from the group consisting of methanol, ethanol, n-propanol, isopropanol, n-butanol, isobutanol, sec-butanol and tetraethylene glycol.

18. The process of claim 14, wherein the material of step (d2) is water.

19. A process for the preparation of caprolactam comprising the following steps:

(a) heating 6-aminocapronitrile, or a mixture comprising 6-aminocapronitrile and water, and a low-boiling or a high-boiling alcohol in the presence of a heterogenous catalyst under superatmospheric pressure in a reactor A to give a mixture I, (b) distilling the mixture I to give a top fraction, caprolactam and a bottom product, (c1) feeding the tour fraction into the reactor A of step (a), and (c1') optionally mixing the top fraction from step (b) with the alcohol water or 6-aminocapronitrile of step (a) before feeding the top fraction into reactor A, (d4) adding water and a base to the bottom product to form a mixture, and then heating said mixture in a reactor D without the addition of a catalyst to give a reacted mixture from which caprolactam is obtained by further distilling.

20. The process of claim 19, wherein mixture I further comprises ammonia, and step (a) further comprises removing the ammonia prior to distillation in step (b).

21. A process for the preparation of caprolactam comprising the following steps:

(a) heating 6-aminocapronitrile, or a mixture comprising 6-aminocapronitrile and water and a low-boiling or a high-boiling alcohol in the presence of a heterogenous catalyst under superatmospheric pressure in a reactor A to give a mixture I, (b) distilling the mixture I to give a top fraction, caprolactam and a bottom product, (c2) feeding the top fraction and optionally the bottom product into a reactor B to obtain a mixture from reactor B, and distilling the mixture from reactor B to yield further caprolactam, and (c2') optionally mixing the top fraction with the alcohol, water, or 6-aminocapronitrile of step (a) before feeding into the reactor B, (d2) adding water and a low-boiling or high-boiling alcohol to the bottom product to form a mixture and heating said mixture in a further reactor C to give a reacted mixture from which caprolactam is obtained by further distilling.

22. A process for the preparation of caprolactam compromising the following steps:

(a) heating 6-aminocapronitrile, or a mixture comprising 6-aminocapronitrile and water and a low-boiling or a high-boiling alcohol in the presence of a heterogenous catalyst under superatmospheric pressure in a reactor A to give a mixture I, (b) distilling the mixture I to give a top fraction, caprolactam and a bottom product, (c2) feeding the top fraction and optionally the bottom product into a reactor B to obtain a mixture from reactor B, and distilling the mixture from reactor B to yield further caprolactam, and (c2') optionally mixing the top fraction with the alcohol, water, or 6-aminocapronitrile of step (a) before feeding into the reactor B, (d3) adding water to the bottom product to form a mixture, and then heating said mixture in a further reactor C to give a reacted mixture from which caprolactam may be obtained by further distilling.

23. A process for the preparation of caprolactam comprising the following steps:

(a) heating 6-aminocapronitrile, or a mixture comprising 6-aminocapronitrile and water and a low-boiling or a high-boiling alcohol in the presence of a heterogenous catalyst under superatmospheric pressure in a reactor A to give a mixture I, (b) distilling the mixture I to give a top fraction, caprolactam and a bottom product, (c2) feeding the top fraction and optionally the bottom product, into a reactor B, and distilling the mixture from reactor B to yield further caprolactam, and (c2') optionally mixing the top fraction with the alcohol, water, or 6-aminocapronitrile of step (a) before feeding into the reactor B, (d4) adding water and a base to the bottom product to form a mixture, and then heating said mixture in a reactor D without the addition of a catalyst to give a reacted mixture from which caprolactam is obtained by further distilling.

* * * * *

UNITED STATES PATENT AND TRADEMARK OFFICE

CERTIFICATE OF CORRECTION

PATENT NO.: 5,874,575

DATED: February 23, 1999

INVENTOR(S): FUCHS et al.

It is certified that error appears in the above-identified patent and that said Letters Patent is hereby corrected as shown below:

Col. 8, claim 1, line 11, delete "caprolantam" and substitute --caprolactam--.

Col. 8, claim 1, line 26, delete "stop" and substitute --step--.

Col. 8, claim 8, line 56, "(C2')" should be --(c2')--.

Col. 9, claim 19, line 50, delete "tour" and substitute --top--.

Signed and Sealed this

First Day of June, 1999

Attest:

Q. TODD DICKINSON

*Attesting Officer*

*Acting Commissioner of Patents and Trademarks*